United States Patent
Liang et al.

(10) Patent No.: US 9,638,406 B1
(45) Date of Patent: May 2, 2017

(54) ENERGY-SAVING DEVICE OF SURGICAL LIGHT

(71) Applicant: Amtai Medical Equipment, Inc., Raleigh, NC (US)

(72) Inventors: Clay Liang, Raleigh, NC (US); Wei-Li Wu, Taichung (TW); Chih-Cheng Tseng, Taoyuan (TW)

(73) Assignee: AMTAI MEDICAL EQUIPMENT, INC., Raleigh, NC (US)

( * ) Notice: Subject to any disclaimer, the term of this patent is extended or adjusted under 35 U.S.C. 154(b) by 0 days.

(21) Appl. No.: 15/058,166

(22) Filed: Mar. 2, 2016

(51) Int. Cl.

| F21V 23/04 | (2006.01) |
| F21V 21/40 | (2006.01) |
| H05B 37/02 | (2006.01) |
| F21V 33/00 | (2006.01) |
| F21Y 105/18 | (2016.01) |
| F21W 131/205 | (2006.01) |

(52) U.S. Cl.
CPC ........ F21V 23/0471 (2013.01); F21V 21/403 (2013.01); F21V 23/0414 (2013.01); F21V 33/0068 (2013.01); H05B 37/0227 (2013.01); F21W 2131/205 (2013.01); F21Y 2105/18 (2016.08)

(58) Field of Classification Search
CPC ............ H05B 33/0803; H05B 33/0815; F21V 21/403; F21V 23/003; F21V 23/04; F21W 2131/20; F21W 2131/202; Y10S 362/804; A61B 2090/308; A61B 90/35

USPC ............ 315/291, 294, 312; 362/804, 249.13, 362/395, 399, 410
See application file for complete search history.

(56) References Cited

U.S. PATENT DOCUMENTS

| 5,497,295 A | * | 3/1996 | Gehly | .................. G02B 6/0006 362/249.09 |
| 6,402,351 B1 | * | 6/2002 | Borders | ..................... F21V 7/09 362/395 |
| 6,863,422 B2 | * | 3/2005 | Jesurun | .................. F21V 21/403 362/295 |
| 7,008,074 B1 | * | 3/2006 | Halm | .................. A61B 1/00016 362/105 |
| 7,513,645 B2 | * | 4/2009 | Marka | ..................... F21S 2/005 362/249.09 |

* cited by examiner

*Primary Examiner* — Haissa Philogene
(74) *Attorney, Agent, or Firm* — Leong C. Lei

(57) ABSTRACT

A energy-saving device of surgical light includes a suspension or support system; a light head carried on the suspension or support system and includes a housing, a grip mounted to the housing for hand holding and moving the light head, multiple light clusters mounted in the housing and each including at least one light source, and multiple detection pairs mounted in the housing and each including an emitter and a receiver, in which the emitter transmits a signal that is reflected by an external object to the receiver to detect the external object at a specific site and a specific distance from the light head; a light source driver operable to drive the light clusters according to the detection result of the detection pairs; and an operation interface connected to the light source driver and configured for energy saving modes of fixed light intensity and compensation light intensity.

4 Claims, 4 Drawing Sheets

ENERGY-SAVING DEVICE OF SURGICAL LIGHT

(a) TECHNICAL FIELD OF THE INVENTION

The present invention relates generally to an innovated energy-saving device of surgical light, and more particularly to controls related to illumination of surgical lights.

(b) DESCRIPTION OF THE PRIOR ART

Known surgical lighting generally comprises multiple light sources or a single light source, which is used in combination with reflector(s) to project light, from different angles, to an operation site in a surgical operation room, in order to reduce the influence on illumination of the operation site of the operation room caused by shadows of heads and shoulders of surgeons and medical personnel. The heads and shoulders of the surgeons are generally close to light heads of the surgical lights and may block a relatively large amount of light. The radiation heat of the light blocked that is cast on the surgeons may cause the surgeons to feel hot and sultry and get sweating, eventually affecting the surgical operations undertaken. The amount of light that is blocked provide no illumination to the operation site and the energy consumed by the lighting is generally dissipated, in the form of heat, from a housing of the light head, leading to an undesired burden to an air conditioning system of the operation room.

For surgical operations that require large incisions, a number of surgeons may be involved and the heads and shoulders of these surgeons may simultaneously block the surgical lighting. Under this condition, increasing light intensity of the surgical lighting may be the only solution. This further highlight the above-discussed problems.

Solutions have been proposed by related researchers to address the above-discussed technical drawbacks. An example is given in US Patent Publication No. 2006/0291204, which provides a solution that requires manually shutting down some of a plurality of lighting modules when light is blocked by the heads and shoulders of surgeons, while illumination parameters of the remaining light modules that have not been shut down.

Such a solution, although helping reduce energy consumption of the surgical lighting, requires manual operations of shutting down and adjusting the lighting. The surgeons must temporarily stop the surgical operation for making such adjustments. This causes inconvenience of use of the surgical lighting.

SUMMARY OF THE INVENTION

The primary object of the present invention is to allow a light source driver of surgical lighting to automatically control the activation and deactivation of light clusters of the surgical lighting and compensation of light intensity according to the locations of the surgeons' heads detected by detection pairs and an energy saving mode set by operation room medical personnel so as to achieve an effect of being easy to use and effectively saving energy.

To achieve the above object, the present invention provides an energy-saving device of surgical light, which comprises: a suspension or support system; one or multiple light heads carried on the suspension or support system, each of the light heads comprising a housing, one or multiple grips mounted to the housing for hand holding and moving the light head to a predetermined location, multiple light clusters mounted in the housing and each comprising at least one light source, and multiple detection pairs mounted in the housing and each comprising an infrared emitter and an infrared receiver, wherein the infrared emitter transmits a signal that is reflected and redirected by an external object to the infrared receiver to detect the external object at a specific site and a specific distance from the light head during a surgical operation; a light source driver connected to operation interfaces, the detection pairs, and the light clusters for driving the light clusters according to settings of each of the operation interface and detection result of each of the detection pairs; and one or multiple operation interface, which are configured with at least energy saving modes of fixed light intensity and compensation light intensity.

In an embodiment of the present invention, the light clusters and the detection pairs are alternately disposed in the housing as a circular array along a center axis of the head light thus making each of the light clusters located between every two detection pairs.

In an embodiment of the present invention, each of the operation interfaces comprises indicators to indicate a status of activation or deactivation for each of the energy saving modes.

In an embodiment of the present invention, each of the operation interfaces comprises a switch that is operable for setting, for each of the energy saving modes, deactivation of some or all.

In an embodiment of the present invention, when the energy saving mode is set as fixed light intensity, the light source driver automatically deactivates some of the light clusters that are blocked by surgeons' heads according to the result of detection made by each of the detection pairs, but does not alter light intensity emitting from the remaining ones of the light clusters so as to achieve an effect of saving energy.

In an embodiment of the present invention, when the energy saving mode is set as compensation light intensity, the light source driver automatically deactivates some of the light clusters that are blocked by surgeons' heads according to the result of detection made by each of the detection pairs and increases the light intensity emitting from the remaining ones of the light clusters in order to maintain stable illumination of an operation site in a surgical operation room.

In an embodiment of the present invention, each of the operation interfaces may shut down both energy saving modes for fixed light intensity and compensation light intensity.

The foregoing objectives and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

DETAILED DESCRIPTION OF THE
PREFERRED EMBODIMENTS

The following descriptions are exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

Figure 1:
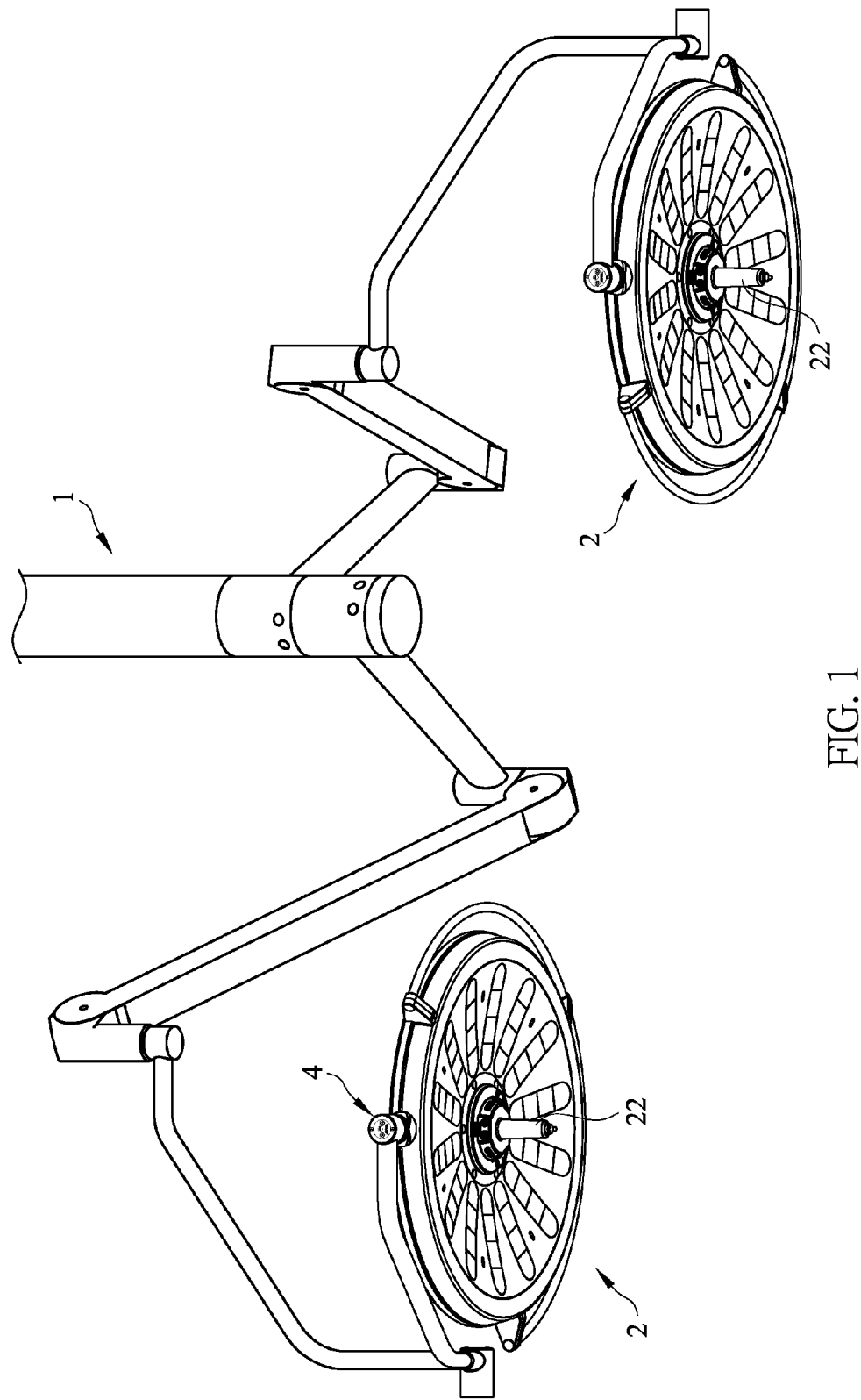
FIG. 1 is a schematic view illustrating an entire arrangement of the present invention.
Figure 2:
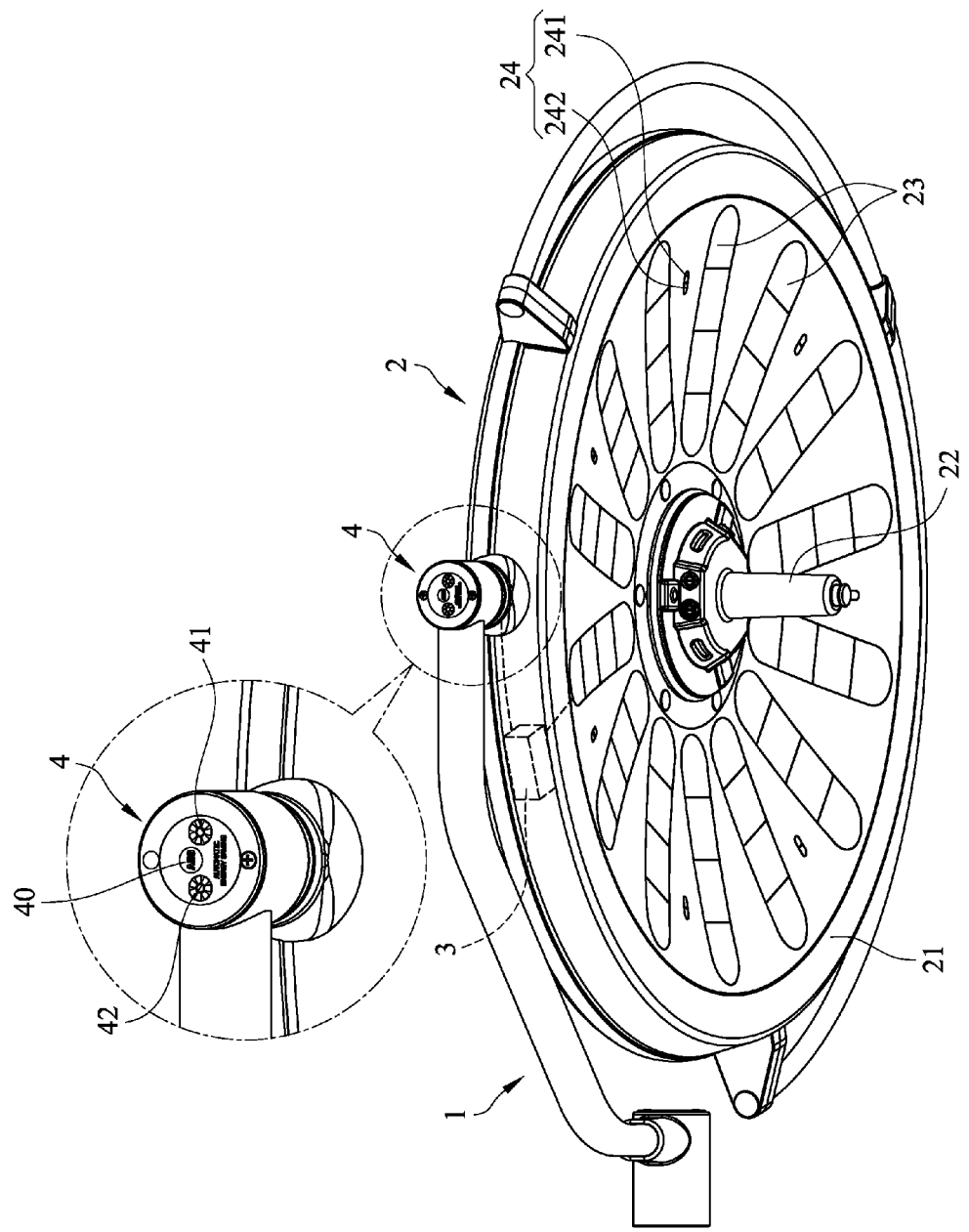
FIG. 2 is a perspective view showing a light head of the arrangement of the present invention.
Figure 3:
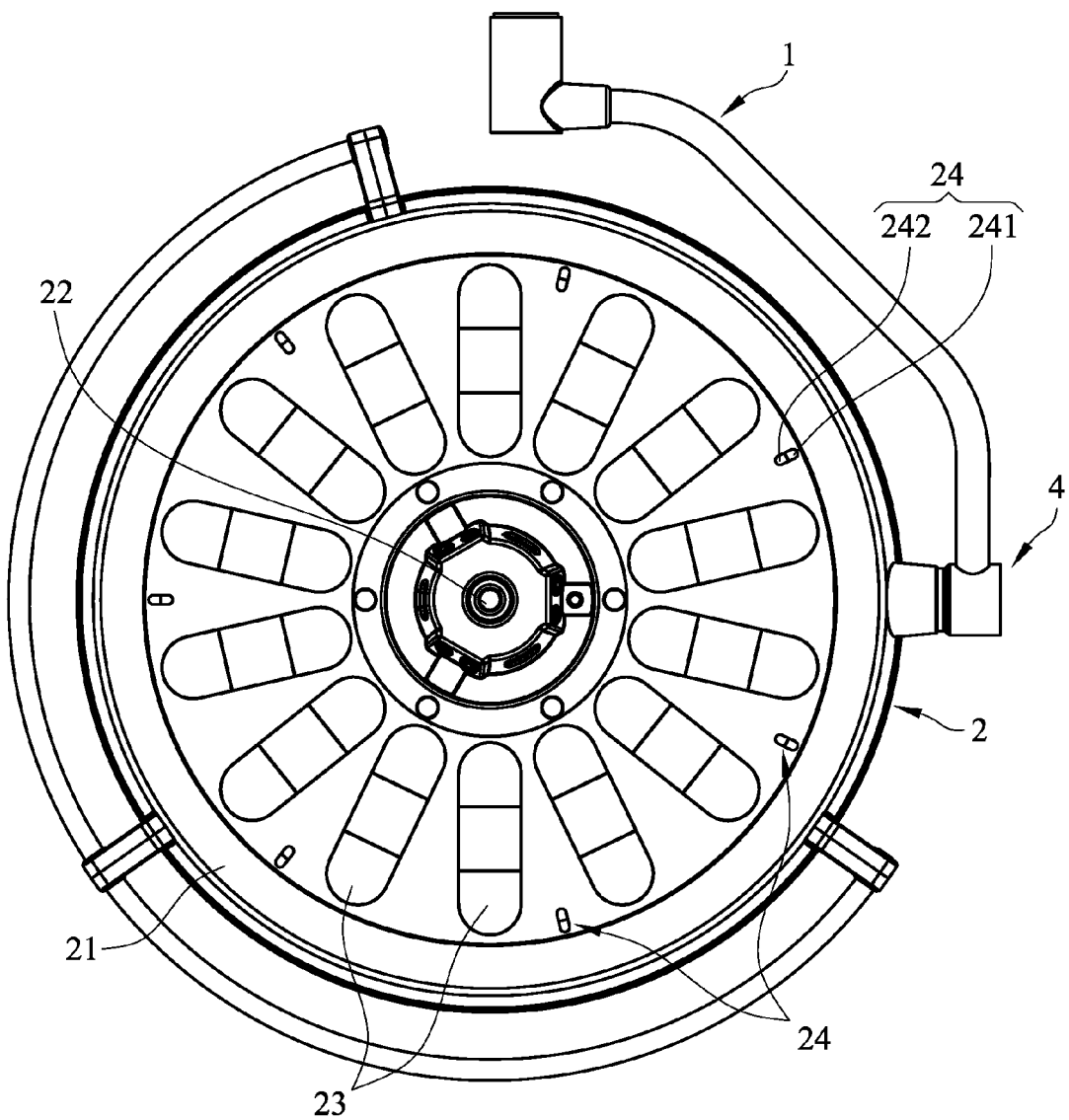
FIG. 3 is a bottom view of the light head of the arrangement of the present invention.
Figure 4:
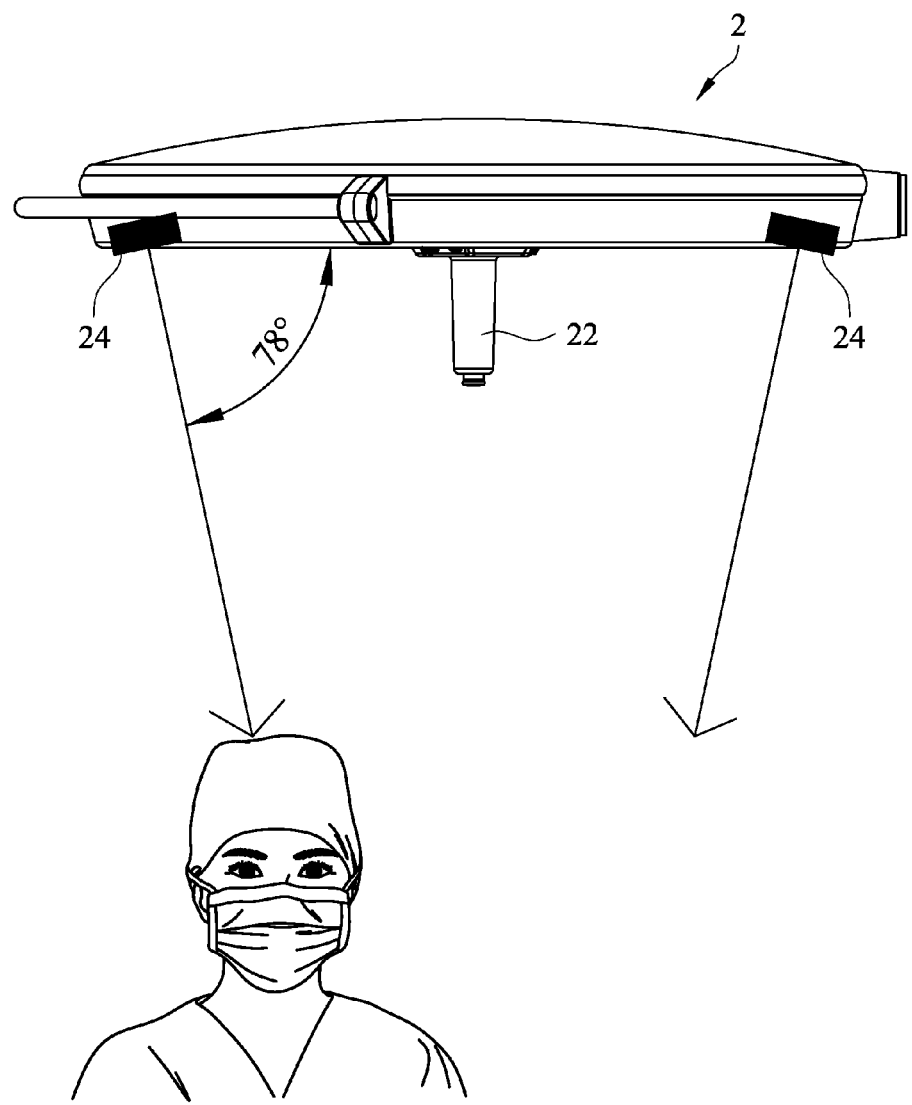
FIG. 4 is a schematic view illustrating the light head of the arrangement of the present invention in a detecting state.

Referring first to FIGS. 1, 2, 3, and 4, which are respectively a schematic view illustrating an entire arrangement of the present invention, a perspective view showing a light head of the arrangement of the present invention, a bottom view of the light head of the arrangement of the present invention, and a schematic view illustrating the light head of the arrangement of the present invention in a detecting state, as shown in the drawings, the present invention provides an energy-saving device of surgical light, which at least comprises:

a suspension or support system 1;

one or multiple light heads 2 carried on the suspension or support system 1 and each comprise a housing 21, one or multiple grips 22 mounted to the housing 21 for hand holding and moving the light heads 2 to a desired location, multiple light clusters 23 mounted in the housing 21 and each comprising at least one light source, multiple detection pairs 24 mounted in the housing 21 and each comprising an infrared emitter 241 and an infrared receiver 242, wherein a signal transmitted from the infrared emitter 241 is reflected and redirected by an external object to the infrared receiver 242 to detect the external object at a specific site and a specific distance from the light head 2 during a surgical operation, wherein the specific site is defined within an included angle of 78 degrees between the detection pair 24 and the light head 2 and the specific distance includes a range of 40 centimeters from the light head 2, wherein the light clusters 23 and the detection pair 24 are alternately disposed in the housing 21 and as a circular array along a center axis of the light head thus making each of the light clusters 23 located between every two detection pairs 24;

a light source driver 3 connected to operation interfaces 4, the detection pairs 24, and the light clusters 23, wherein the light source driver 3 automatically drives the light clusters 23 according to settings of each of the operation interfaces 4 and detection result of each of the detection pairs 24;

one or multiple operation interfaces 4, wherein each of the operation interfaces 4 comprises a switch 40 and is configured for setting at least an energy saving mode of fixed light intensity or compensation light intensity by means of the switch 40, wherein when a mode of fixed light intensity is set, the light source driver 3 automatically deactivates some of the light clusters 23 according to the detection result of each of the detection pairs 24, but does not alter the light intensity emitting from the remaining ones of the light clusters 23; and when a mode of compensation light intensity is set, the light source driver 3 automatically deactivates some of the light clusters 23 according to the detection result of each of the detection pairs 24 and increases the light intensity emitting from the remaining ones of the light clusters 23; alternately, each of the operation interfaces 4 may simultaneously shut down the energy saving modes of fixed light intensity and compensation light intensity, each of the operation interfaces 4 comprising indicators 41, 42, for indicating the state of activation or deactivation of each of the energy saving modes.

When the present invention is put into use, surgical operation room medical personnel may use the switch 40 of each of the operation interfaces 4 to set the fixed light intensity or the compensation light intensity or to disable the energy saving mode. Details are provided below:

When the surgical lighting is initially put into operation, the right-side indicator 41 of each of the operation interfaces 4 is lit and the fixed light intensity mode is started; however, no light compensation is performed. Under this condition, if the detection pairs 24 detect situation of light being blocked, the light clusters 23 located in some of sections are deactivated, and no light compensation is carried out on the light clusters 23 of the remaining sections; through pressing down the switch 40 of each of the operation interfaces 4, the left-side indicator 42 is lit and operation is switched to the compensation light intensity mode, which starts up light compensation, so that when the detection pairs 24 detect a situation of light being blocked, the light clusters 23 of some of the sections are deactivated, while light compensation is carried out on the light clusters 23 of the remaining sections; through pressing down the switch 40 of each of the operation interfaces 4 again, both indicators 41, 42 are turned off and the operation is switched to a disabled mode, where no detection is performed by the detection pairs 24 and no compensation of light is performed. As such, an easy way of operation is provided. After the settings are made, the detection pairs 24 start operations of detection so that the infrared emitter 241 continuously transmits a signal (however, the infrared receiver 242 is not in an operation of receiving the signal). During the process of a surgical operation, when the head or the shoulders of a surgeon gets into a distance of approximately 40 centimeters from the light heads 2 and block the signal transmitted from the infrared emitter 241, the signal so blocked is reflected and redirected to the infrared receiver 242, so that the result of detection is transmitted to the light source driver 3, which follows the fixed light intensity mode or the compensation light intensity mode set in advance to control the light intensity of each of the light clusters 23 to achieve an effect of saving energy.

The three modes of lighting, including fixed light intensity, compensation light intensity, and disabling, are respectively described as follows:

(1) For the fixed light intensity mode, the light source driver 3 automatically deactivates some of the light clusters 23 according to the detection result of each of the detection pairs 24, but does not alter the light intensity emitting from the remaining ones of the light clusters 23 so that the light clusters 23 that are not deactivated exhibit the fixed light intensity mode and such a mode shuts down the lighting of the light clusters 23 that are blocked by the heads and/or the shoulders of the surgeons, wherein due to pupils expanding when illumination gets lowered down, deactivating some of the lighting does not actually affect the vision of the surgeons during the process of a surgical operation.

(2) For the compensation light intensity mode, the light source driver 3 automatically deactivates some of the light clusters 23 according to the detection result of each of the detection pairs 24 and increases the light intensity emitting from the remaining ones of the light clusters 23 so that the lighting of the light clusters 23 that are blocked by the heads and/or shoulders of the surgeons is deactivated, while the remaining ones of the light clusters 23 are subjected to adjustment to increase the light intensity emitting therefrom, wherein when a surgical operation involves a relatively large size of incisions and a number of surgeons who do the operation together may have their heads and/or shoulders block the lighting of the light clusters 23 at the same time, the light intensity is increased only for those light sources that are not blocked to allow for maintenance of sufficient illumination for the operation site but not increasing the illumination of the surgical lighting.

(3) For setting of either the fixed light intensity mode or the compensation light intensity mode, when the switch 40 of each of the operation interfaces 4 is simultaneously shut down, the disabled mode is entered, wherein when the patient is operated with only a small size incision but deep invasion (such as operations made in the neck or the throat), light that travels deeply into the bottom of the incision is that comes around a periphery of the head of a surgeon and for setting of both the fixed light intensity mode and the compensation light intensity mode would cause undesired loss of the light coining around the head of the surgeon, so that both the fixed light intensity mode and the compensation light intensity mode must be deactivated.

Since each of the light clusters 23 is arranged between every two of the detection pair 24, when the fixed light intensity mode or the compensation light intensity mode is activated, two adjacent ones of the detection pair 24 detect the reflection signals of their own at the same time so that it only needs to deactivate all light clusters 23 located between every two of the detection pairs 24, avoiding deactivation of only some of the light clusters 23 of which lighting therefrom is blocked.

In summary, the present invention provides an energy-saving device of surgical light that effectively overcome the shortcoming of the prior art and may allow a light source driver of surgical lighting to automatically control the activation and deactivation of each of the light clusters of the surgical lighting and compensation of light intensity according to the locations of the surgeons' heads detected by detection pairs and an energy saving mode set by operation room medical personnel so as to achieve an effect of being easy to use and effectively saving energy.

It will be understood that each of the elements described above, or two or more together may also find a useful application in other types of methods differing from the type described above.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the claims of the present invention.

I claim:

1. A surgical light, comprising:
   a suspension or support system;
   one or multiple light heads carried on the suspension or support system, wherein each of the light heads comprises a housing, one or multiple grips mounted to the housing for hand holding and moving the light head to a predetermined location, multiple light clusters mounted in the housing and each comprising at least one light source, and multiple detection pairs mounted in the housing and each comprising an infrared emitter and an infrared receiver, wherein the infrared emitter transmits a signal that is reflected and redirected by an external object to the infrared receiver to detect the external object at a specific location and a specific distance from the light head during surgery;
   a light source driver connected to operation interfaces, the detection pairs, and the light clusters for driving the light clusters according to settings of each of the operation interfaces and detection result of each of the detection pairs; and
   one or multiple operation interfaces, which are each configured with at least energy saving modes of fixed light intensity and compensation light intensity, wherein when a mode of fixed light intensity is set, the light source driver automatically deactivates some of the light clusters according to the detection result of each of the detection pairs, but does not alter light intensity emitting from the remaining ones of the light clusters; and when a mode of compensation light intensity is set, the light source driver automatically deactivates some of the light clusters according to the detection result of each of the detection pairs and increases the light intensity emitting from the remaining ones of the light clusters.

2. The surgical light according to claim 1, wherein each of the operation interfaces is operable to shut down both energy saving modes of fixed light intensity and compensation light intensity.

3. The surgical light according to claim 2, wherein each of the operation interfaces comprises indicators to indicate a status of activation or deactivation for each of the energy saving modes.

4. The surgical light according to claim 3, wherein the light clusters and the detection pairs are alternately disposed in the housing as a circular array along the center axis of the light head thus making each of the light clusters located between every two detection pairs.

* * * * *